(12) United States Patent
Ruoslahti et al.

(10) Patent No.: US 6,177,542 B1
(45) Date of Patent: *Jan. 23, 2001

(54) INTEGRIN-BINDING PEPTIDES

(75) Inventors: Erkki Ruoslahti, Rancho Santa Fe; Erkki Koivunen, San Diego, both of CA (US)

(73) Assignee: The Burnham Institute, San Diego, CA (US)

( * ) Notice: Under 35 U.S.C. 154(b), the term of this patent shall be extended for 0 days.

This patent is subject to a terminal disclaimer.

(21) Appl. No.: 08/924,002

(22) Filed: Aug. 29, 1997

Related U.S. Application Data

(62) Division of application No. 08/625,695, filed on Apr. 3, 1996, now Pat. No. 5,912,234, which is a continuation of application No. 08/212,186, filed on Mar. 11, 1994, now Pat. No. 5,536,814, which is a continuation-in-part of application No. 08/127,422, filed on Sep. 27, 1993, now abandoned.

(51) Int. Cl.$^7$ .................................................. C07K 7/00
(52) U.S. Cl. ...................... 530/326; 530/300; 530/317; 530/324; 530/325; 530/327; 530/328; 530/329; 530/330
(58) Field of Search .................................. 530/300, 317, 530/324, 325, 326, 327, 328, 329, 330

(56) References Cited

U.S. PATENT DOCUMENTS

| 5,192,746 | 3/1993 | Lobl et al. ............................. 514/11 |
| 5,262,520 | 11/1993 | Plow et al. ........................... 530/326 |
| 5,536,814 | * 7/1996 | Ruoslahti et al. .................... 530/329 |

FOREIGN PATENT DOCUMENTS 410537   1/1991  (EP) .

OTHER PUBLICATIONS

Presta et al., J. Cell. Physiol. 149:512–524, 1991.*
Bauer et al., "Motility of Fibronectin Receptor–Deficient Cells on Fibronectin and Vitronectin: Collaborative Interactions Among Integrins", *J. Cell Biol.*, 116:477–487 (1992).
Buck et al., "Review Integrin–Mediated Cell Adhesion," *J. Cell Sci. Suppl.* 8:231–250 (1987).
Carbone et al., The Use of Hydrophobic, α–Helix–Defined Peptides in Delineating the T Cell Determinant for Pigeon Cytochrome cl:, *J. Immunol.*, 138:1838–1844 (1987).
Dedhar et al., "A Cell Surface Receptor Complex for Collagen Type I Recognizes the Arg–Gly–Asp Sequence," *J. Cell Biol.*, 104:585–593 (1987).
Freed et al., "A Novel Integrin β subunit is Associated with the Vitronectin Receptor α Subunit (αv) in a Human Osteosarcoma Cell Line and is a Substrate for Protein Kinase C," *EMBO J.*, 8:2955–2965 (1989).
Giancotti and Ruoslahti, "Elevated Levels of the α5β1 Fibronectin Receptor Suppress the Transformed Phenotype of Chinese Hamster Ovary Cells," *Cell*, 60:849–859 (1990).

Koivunen et al., "Isolation of a Highly Specific Ligan for the $\alpha_5\beta_1$ Integrin from a Phage Display Library," *J. Cell. Biol.*, 124:373–380 (1994).
Koivunen et al., "Selection of Peptides Binding to the $\alpha_5\beta_1$ Integrin from Phage Display Library," *J. Biol. Chem.*, 268:20205–20210 (1993).
Morla and Ruoslahti, "A Fibronenctin Self–Assembly Site Involved in Fibronectin Matrix Assembly: Reconstruction in a Synthetic Peptide," *J. Cell Biol.*, 118:421–429 (1992).
Pierschbacher and Ruoslahti, "Cell Attachment Activity of Fibronectin can be Duplicated by Small Synthetic Fragments of the Molecule," *Nature*, 309:30–33 (1984).
Pytela et al., "A 125/115–kDa Cell Surface Receptor Specific for Vitronectin Interacts with the Arginine–Glycine–Aspartic Acid Adhesion Sequence Derived from Fibronectin", *PNAS USA*, 82:5766–5770 (1985).
Pytela et al., "Arginine–Glycine–Asparatic–Acid Adhesion Receptors," *Methods Enzymol.*, 144:475–489 (1987).
Pytela et al., "Identification and Isolation of a 140 kd Cell Surface Glycoprotein with Properties Expected of a Fibronectin Receptor", *Cell*, 40:191–198 (1985).
Rhodes and Miller, "Physicochemical Characterization and Molecular Organization of the Collagen A and B Chains," *Biochem*, 17:3442–3448 (1978).
Ruoslahti et al., "Fibronectin: Purification, Immunochemical Properties, and Biological Activities," *Methods Enzymol.*, 82:803–831 (1982).
Scott and Smith, "Searching for Peptide Ligands with an Epitope Library," *Science*, 249:386–390 (1990).
Smith and Scott, "Libraries of Peptides and Proteins Displayed on Filamentous Phage," *Methods Enzymol.*, 217:228–257 (1993).
Vogel et al., "A Novel Integrin Specificity Exemplified by Binding of the $\alpha v\beta 5$ Integrin to the Basic Domain of the HIV Tat Protein and Vitronectin," *J. Cell Biol.*, 121:461–468 (1993).
Yamada et al., "Recent Advances in Research on Fibronectin and Other Cell Attachment Proteins", *J. Cell. Biochem.*, 28:79–97 (1985).
Zhang et al., "The $\alpha v\beta 1$ Integrin Functions as a Fibronectin Receptor but does not Support Fibronectin Matrix Assembly and Cell Migration on Fibronectin," *J. Cell Biol.*, 122:235–242 (1993).

* cited by examiner

*Primary Examiner*—Christopher S. R. Low
*Assistant Examiner*—Enrique D. Longton
(74) *Attorney, Agent, or Firm*—Campbell & Flores LLP

(57) ABSTRACT

The present invention provides peptides having specificity for fibronectin-binding and vitronectin-binding integrins, and in particular for $\alpha_5\beta_1$ integrin. These peptides are characterized by having the ability to interfere with extracellular matrix protein binding to integrins; to block attachment of cells expressing these integrins to extracellular matrix proteins; and to promote cell attachment when coated onto a surface.

1 Claim, 4 Drawing Sheets

INTEGRIN-BINDING PEPTIDES

This application is a divisional application of U.S. Ser. No. 08/625,695, now U.S. Pat. No. 5,912,234 filed Apr. 3, 1996, which is a continuation of U.S. Ser. No. 08/212,186, Mar. 11, 1994, now U.S. Pat. No. 5,536,814, issued Jul. 16, 1996, which is a continuation-in-part of U.S. Ser. No. 08/127,422, filed Sep. 27, 1993, now abandoned, which is herein incorporated by reference.

This invention was made with government support under grants CA45207, CA28896 and Cancer Center Support Grant CA30199 awarded by the National Institutes of Health. The government has certain rights to this invention.

BACKGROUND OF THE INVENTION

Integrins are transmembrane $\alpha\beta$ heterodimer receptors expressed on a wide variety of cells which are involved in extracellular matrix interactions. There are eight known $\beta$ subunits and 14 known $\alpha$ subunits which associate with each other to give at least twenty receptors with different ligand specificities. The ligands for several of the integrins are adhesive extracellular matrix (ECM) proteins such as fibronectin, vitronectin, collagens and laminin.

It is becoming increasingly clear that the ECM influences gene expression and changes in expression of genes encoding matrix proteins alter the composition of the ECM. Integrins appear to mediate messages from the exterior to the interior of the cell, inducing various kinds of changes in gene expression. In this capacity, the integrins control many medically important biological phenomena, such as cell migration in development, tissue repair, cancer cell differentiation, platelet aggregation and homing of immune system cells and neuronal processes to target sites.

Many integrins recognize the amino acid sequence RGD (arginine-glycine-aspartic acid) which is present in fibronection or the other adhesive proteins to which they bind. Peptides and protein fragments containing the RGD sequence can be used to modulate the activities of the RGD-recognizing integrins. While apparently successful drugs and devices have been designed based on the RGD sequence for antithrombotic therapy, wound healing and implant acceptance, a limitation of this approach is that RGD peptides not subject to conformational restraint tend to be nonselective in their integrin binding.

Fibronectin is the only known protein ligand for the $\alpha_5\beta_1$ integrin. This binding is mediated through an RGD (Arginine-Glycine-Aspartic Acid) sequence. In contrast, the integrins $\alpha_v\beta_3$ and $\alpha_{IIb}\beta_3$, which also recognize the RGD sequence, are capable of binding many different adhesive proteins.

The $\alpha_5\beta_1$ integrin is important in promoting the assembly of fibronectin matrix and initiating cell attachment to fibronectin. The $\alpha_5\beta_1$ integrin also appears to be a crucial integrin mediating migration of cells.

The use of ligands with specificity for the $\alpha_5\beta_1$ receptor permit modulation and manipulation of cell migration in situations such as wound healing, tissue repair and tumor invasion. Thus, there is a need to develop drug-like ligands that bind effectively and selectively to an individual integrin. This invention satisfies this need by providing novel peptides that have improved affinities and selectivities for integrins, particularly the $\alpha_5\beta_1$ integrin.

SUMMARY OF THE INVENTION

The present invention provides peptides recognized by fibronectin-binding and vitronectin-binding integrins, and in particular by $\alpha_5\beta_1$ integrin. These peptides are characterized by their ability to interfere with fibronectin and vitronectin binding to various integrins and to block integrin-mediated cell attachment to extracellular matrix proteins. When immobilized onto a surface, these peptides can promote cell attachment through integrin binding.

DETAILED DESCRIPTION OF THE INVENTION

Figure 1:
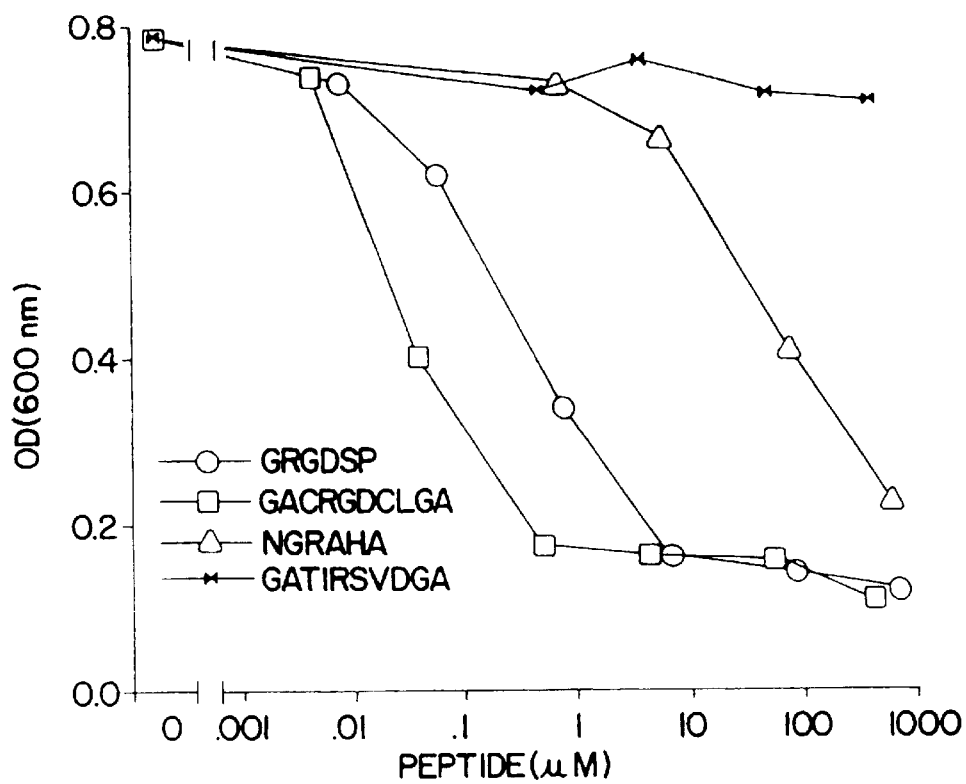
FIG. 1 shows the inhibition of CRGDCL (SEQ ID NO 1)-phage binding to $\alpha_5\beta_1$ integrin by the peptides GRGDSP (SEQ ID NO 2), GACRGDCLGA (SEQ ID NO 3), NGRAHA (SEQ ID NO 4) and GATIRSVDGA (SEQ ID NO 5).

The present invention provides peptides recognized by fibronectin- and vitronectin-binding integrins, in particular by the $\alpha_5\beta_1$ integrin. These peptides include in their sequence one of several peptide motifs which have been identified as binding to $\alpha_5\beta_1$ integrin. These motifs include the following amino acid sequences: DGR, NGR, and CRGDC (SEQ ID NO 10).

The peptides of the present invention are characterized by their ability to inhibit integrin-expressing cells from binding to extracellular matrix proteins, and in particular the binding of fibronectin to $\alpha_5\beta_1$ integrin. Embodiments include the linear or cyclic peptide motifs CRGDCL (SEQ ID NO:01), NGR(AHA) and DGR(AHA) (SEQ ID NO 11). The CRGDCL (SEQ ID NO:02) peptide binds with a higher affinity than the previously described RGD peptides to all of the RGD-directed integrins tested. Its wide specificity and affinity make it useful as a general inhibitor and mediator of RGD-dependent cell attachment.

Both the NGR(AHA) and DGR(AHA) peptides contain the AHA sequence, which is not essential for binding, as indicated by the parentheses surrounding this sequence. The NGR sequence shows some selectivity toward the $\alpha_v\beta_5$ integrin.

The DGR sequence portion of the DGRAHA peptide has been previously described as a part of the SDGR (SEQ ID NO 12) peptide (Yamada et al., *J Cell Biochem* 28: 97–97 (1985)). However, it has since been demonstrated that the SDGR peptide is essentially inactive as a binding peptide. In contrast, peptides having aspartic acid residue (D) at the N-terminus, such as DGR, are found to have integrin binding activity. DGR-containing peptides with D at the N-terminus also show some selectivity for the $\alpha_v\beta_5$ integrin.

As used herein, the term "amino acid" and any reference to a specific amino acid is meant to include naturally occurring proteogenic amino acids as well as non-naturally occurring amino acids such as amino acid analogs. One of skill in the art would know that this definition includes, unless otherwise specifically indicated, naturally occurring proteogenic (D) or (L) amino acids, chemically modified amino acids, including amino acid analogs such as penicillamine (3-mercapto-D-valine), naturally occurring non-proteogenic amino acids such as norleucine and chemically synthesized compounds that have properties known in the art to be characteristic of an amino acid. As used herein, the term "proteogenic" indicates that the amino acid can be incorporated into a protein in a cell through well-known metabolic pathways.

The choice of including an (L)- or a (D)- amino acid into a peptide of the present invention depends, in part, on the desired characteristics of the peptide. For example, the incorporation of one or more (D)-amino acids can confer increasing stability on the peptide in vitro or in vivo. The incorporation of one or more (D)-amino acids also can increase or decrease the binding activity of the peptide as determined, for example, using the binding assays described herein, or other methods well known in the art. In some cases it is desirable to design a peptide which retains activity for a short period of time, for example, when designing a peptide to administer to a subject. In these cases, the incorporation of one or more (L)-amino acids in the peptide can allow endogenous peptidases in the subject to digest the peptide in vivo, thereby limiting the subject's exposure to an active peptide.

As used herein, the term "amino acid equivalent" refers to compounds which depart from the structure of the naturally occurring amino acids, but which have substantially the structure of an amino acid, such that they can be substituted within a peptide which retains is biological activity. Thus, for example, amino acid equivalents can include amino acids having side chain modifications or substitutions, and also include related organic acids, amides or the like. The term "amino acid" is intended to include amino acid equivalents. The term "residues" refers both to amino acids and amino acid equivalents.

As used herein, the term "peptide" is used in its broadest sense to refer to compounds containing amino acid equivalents or other non-amino groups, while still retaining the desired functional activity of a peptide. Peptide equivalents can differ from conventional peptides by the replacement of one or more amino acids with related organic acids (such as PABA), amino acids or the like or the substitution or modification of side chains or functional groups.

It is to be understood that limited modifications can be made to a peptide without destroying its biological function. Thus, modification of the peptides of the present invention that do not completely destroy their activity are within the definition of the compound claims as such. Modifications can include, for example, additions, deletions, or substitutions of amino acids residues, substitutions with compounds that mimic amino acid structure or functions, as well as the addition of chemical moieties such as amino or acetyl groups. The modifications can be deliberate or accidental, and can be modifications of the composition or the structure.

As used herein, "binding" refers to the ability of a given peptide to interact with an integrin such that the interaction between the peptide and integrin is relatively specific. As used herein, the term "relatively specific" means that the affinity of binding of the integrin and peptide is about $1\times10^{-5}$ M or less. Therefore, the term "binding" does not encompass non-specific binding, such as non-specific adsorption to a surface. Non-specific binding can be readily identified by including the appropriate controls in a binding assay. Methods for determining the binding affinity are described in the Examples below.

A distinctive characteristic of such binding is that the bound peptide can be detached or prevented from binding to an integrin by initial contact with, or specific elution with, the fibronectin-derived synthetic GRGDSP peptide (see Pytela et al. *Cell* 40: 191–198 (1985), and Pytela et al. *Proc. Natl. Acad Sci USA* 82: 5766–5770 (1985), each of which are incorporated herein by reference). In addition, specific binding can be disrupted using an agent such as EDTA, which renders an integrin inactive, or by a nonspecific protein denaturant such as low pH buffer, as described in the procedure set out in the Examples below.

Using the binding assays described herein and other binding assays well known in the art, the relative binding affinity of a peptide for an integrin can be determined. As used herein, the term "relative binding affinity" refers to the ability of one peptide, in comparison to a second peptide, to inhibit the binding to an integrin of an RGQ peptide such as GRGDSP (SEQ ID NO:02) (see Examples below). The relative binding affinity of a peptide is determined by competitive binding assays which identify peptide motifs which can inhibit the binding of a peptide to an integrin. The relative binding affinities of various peptides of the present invention can be compared by determining the half-maximal inhibitory concentration ($IC_{50}$) of these peptides. Such assays are described in detail in the Example below. Typically, peptides are compared with the standard integrin-binding peptide such as the fibronectin-derived peptide GRGDSP (SEQ ID NO:02). Competitive binding assays using peptides displayed on phage obtained from phage display libraries, such as the phage display library described in Scott and Smith, *Science* 249:1738–1740 (1990) (which is herein incorporated by reference) can also be employed to determine relative binding affinities.

As used herein the term "high binding affinity" refers to peptides which have an $IC_{50}$ of $1\times10^{-7}$ M or less in a competitive binding assay for integrin (see Examples below). Peptides having a high binding affinity are characterized by the ability to bind integrins immobilized on a surface at very low concentrations such as about 10 ng/well.

As used herein the term "selectively binding" or "selectively binds" refers to a peptide which has a high binding affinity, exclusively or predominately, to a designated integrin. Such selective binding can be determined, for example, by inhibition of binding of an RGD-containing peptide to a particular integrin, such as the $\alpha_5\beta_1$ integrin, but not to other integrins.

The peptides of the present invention can be synthesized by using well known methods including recombinant methods and chemical synthesis. Recombinant methods of producing a peptide through the introduction of a vector including nucleic acid encoding the peptide into a suitable host cell is well known in the art, such as is described in Sambrook et al., Molecular Cloning: A Laboratory Manual, 2d Ed, Vols 1 to 8, Cold Spring Harbor, N.Y. (1989), which is herein incorporated by reference. A linear sequence is synthesized, for example, by the solid phase peptide synthesis of Merrifield (Merrifield et al., *J. Am. Chem. Soc.,* 85:2149 (1964), which is incorporated herein by reference). Alternatively, a peptide of the present invention can be synthesized using standard solution methods well known in the art (see, for example, Bodanszky, M., Principles of Peptide Synthesis (Springer-Verlag, 1984)), which is herein incorporated by reference). Newly synthesized peptides can be purified, for example, by high performance liquid chromatography (HPLC), and can be characterized using, for example, mass spectrometry or amino acid sequence analysis.

The peptides of the present invention are particularly useful when they are maintained in a constrained secondary conformation. As used herein, the terms "constrained secondary structure," "stabilized" and "conformationally stabilized" indicate that the peptide bonds comprising the peptide are not able to rotate freely but instead are maintained in a relatively fixed structure.

Various methods for constraining the secondary structure of a peptide are well known in the art. For example, peptides such as the NGR(AHA) and DGR(AHA) can be stabilized into a constrained secondary structure by incorporating the peptide into a larger peptide sequence that forms a known secondary structure. For example, a peptide of the present invention can be stabilized by incorporating it into a sequence that forms a helix such as an alpha helix or a triple helix, according to methods described, for example, by Dedhar et al., *J. Cell. Biol.* 104:585 (1987); by Rhodes et al., *Biochem* 17:3442 (1978); and by Carbone et al., *J. Immunol* 138:1838 (1987), each of which is incorporated herein by reference. Additionally, the peptides can be incorporated into larger linear, cyclic or branched peptides, so long as their integrin-binding activity is retained. The peptides of the present invention may be of any size so long as the integrin-binding activity is retained, however, in one embodiment, peptides having twenty or fewer total amino acids are preferred.

A preferred method for constraining the secondary structure of a newly synthesized linear peptide is to cyclize the peptide using any of various methods well known in the art. For example, a cyclized peptide of the present invention can be prepared by forming a peptide bond between non-adjacent amino acid residues as described, for example, by Schiller et al., *Int. J. Pept. Prot. Res.* 25:171 (1985), which is incorporated herein by reference. Peptides can be synthesized on the Merrifield resin by assembling the linear peptide chain using $N^{\alpha}$-Fmoc-amino acids and Boc and tertiary-butyl proteins. Following the release of the peptide from the resin, a peptide bond can be formed between the amino and carboxy termini.

A newly synthesized linear peptide can also be cyclized by the formation of a bond between reactive amino acid side chains. For example, a peptide containing a cysteine-pair can be synthesized and a disulfide bridge can be formed by oxidizing a dilute aqueous solution of the peptide with $K_3[Fe(CN)_6]$. Alternatively, a lactam such as an $\epsilon(\gamma$-glutamyl)-lysine bond can be formed between lysine and glutamic acid residues, a lysinonorleucine bond can be formed between lysine and leucine residues or a dityrosine bond can be formed between two tyrosine residues. Cyclic peptides can be constructed to contain, for example, four lysine residues, which can form the heterocyclic structure of desmosine (see, for example, Devlin, *Textbook of Biochemistry* 3rd ed. (1992), which is herein incorporated by reference). Methods for forming these and other bonds are well known in the art and are based on well known rules of chemical reactivity (Morrison and Boyd, Organic Chemistry, 6th Ed. (Prentice Hall, 1992), which is herein incorporated by reference).

The present invention provides peptides recognized by fibronectin- and vitronectin-binding integrins, and in particular, peptides recognized by $\alpha_5\beta_1$ integrin. The peptide motifs of the present invention which are recognized by fibronectin- and vitronectin-binding integrins can be initially identified by any number of selection processes. Peptides having a binding affinity for an integrin such as the $\alpha_5\beta_1$ integrin can be identified by screening potential peptides for binding to integrins coated on a surface or contained in a column, for example. This screening can be accomplished, for example, using a degenerate peptide phage display library. Peptides which bind to integrin-coated surfaces can then be eluted using a low pH buffer, the synthetic fibronectin-derived GRDGSP peptide, or a buffer containing EDTA. The eluted peptides can then be characterized. High binding affinity peptides can be selected after this first selection process by re-selecting peptides capable of binding increasingly lower concentrations of $\alpha_5\beta_1$ integrin. Linear as well as cyclic peptide motifs were identified in this manner.

The relative binding affinities of the peptide motifs identified in this manner were then determined by competitive binding assays between the various peptides or between known ligands for binding to $\alpha_5\beta_1$ and $\alpha_v\beta_3$ integrins, for example, as described in the Examples below. High affinity peptides identified in this way include the cyclic peptides CRGDCL (SEQ ID NO:01) and CRGDC (SEQ ID NO:10). Peptides with moderate affinities include CVLNGRME (SEQ ID NO 13) and the linear peptides NGRAHA (SEQ ID NO:04) and DGRAHA (SEQ ID NO:11). Of these peptides, CRGDCL (SEQ ID NO:01) has a high binding affinity for both $\alpha_5\beta_1$ and $\alpha_v\beta_3$ integrins, about 10 times higher as judged by the $IC_{50}$ value compared with similar linear peptides.

Figure 2:
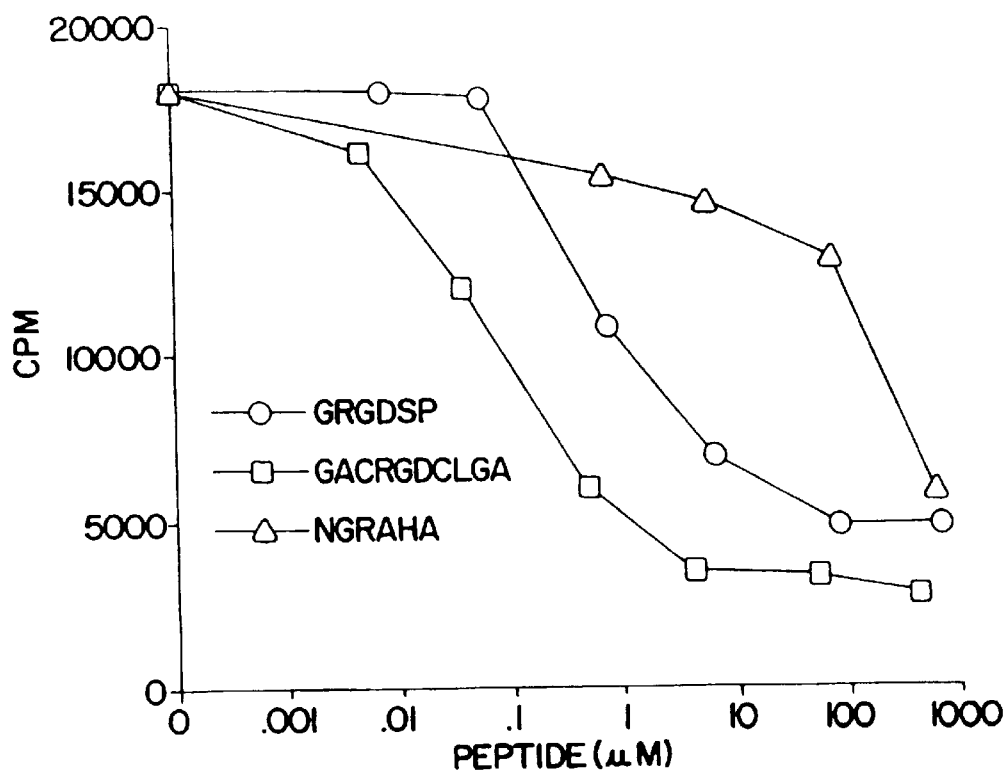
FIG. 2 shows the inhibition of binding of fibronectin to $\alpha_5\beta_1$ integrin by the peptides GRGDSP (SEQ ID NO:02), GACRGDCLGA (SEQ ID NO:03) and NGRAHA (SEQ ID NO:04).

Peptides including these critical motifs were further characterized to determine if they inhibit fibronectin binding to integrins. CRGDCL (SEQ ID NO:01) is very effective at inhibiting fibronectin binding to $\alpha_5\beta_1$ integrin, as shown in FIG. 2 and described in the Example below. The peptides are also characterized by the ability to inhibit the binding of integrin-expressing cells to fibronectin or vitronectin, as described in detail in the Examples below. As can be seen in FIG. 4, the cyclic peptide CRGDCL (SEQ ID NO:01), flanked by the sequence GA, is the most effective peptide at inhibiting the binding of both fibronectin and vitronectin to the integrin-expressing cells. In addition, conformationally constrained peptides have an improved affinity for integrins. The NGR sequence, for example, has a higher activity when present in a cyclic peptide.

Additional peptides of the present invention which have been shown to bind $\alpha_5\beta_1$ integrin are those which include the peptide motifs RCDVVV (SEQ ID NO 14), SLIDIP (SEQ ID NO 15), and TIRSVD (SEQ ID NO 16). Peptides of the present invention which have been shown to preferentially bind $\alpha_5\beta_1$ integrin include the following motifs: KRGD (SEQ ID NO 17), RRGD (SEQ ID NO 18), and RGDL (SEQ ID NO 19).

The $\alpha_5\beta_1$-binding sequences that do not contain the RGD or NGR motif could be categorized into three main groups. Each group showed some homology to sequences present in the 9th and 10th type three repeat of fibronectin. The homologous sequences occurred at analogous positions in each of the type three repeats. These fibronectin sequences are likely to reside in exposed loop regions based on the known structure of the 10th type three repeat. The sequences in the 9th type three repeat could represent a synergistically acting region of fibronectin that was deduced by site-directed mutagenesis and antibody mapping studies of fibronectin. Based on these findings, the fibronectin interaction with $\alpha_5\beta_1$ appears to be mediated by cumulative binding of several loop regions of the type three repeats. The RGD loop-mediated interaction is no doubt the strongest but the NGR and other loops may provide the signal for specific recognition of fibronectin $\alpha_5\beta_1$.

Because of their ability to bind to integrins, the peptides of the present invention can be used to prevent integrin-expressing cells from binding to fibronectin or vitronectin by administering a sufficient quantity of the appropriate peptide to the cells. Such quantities can be determined from the data of FIG. 4, for example. This method is useful for inhibiting metastasis since fibronectin adhesion is linked to metastasis. The peptides of the instant invention can also be used, for example, to inhibit $\alpha_v\beta_1$-mediated cell attachment to fibronectin, and $\alpha_v\beta_5$-mediated cell attachment to vitronectin.

The peptides of the present invention also can be used to promote attachment of integrin-expressing cells to a surface or artificial cell matrix by coating the surface with the peptides, or alternatively, incorporating the peptide into the artificial matrix. The peptides of the present invention are particularly useful because they are readily and inexpensively synthesized and, therefore, are more readily available, for example, than antibodies specific for an integrin or integrin subunits. For example, the peptides can be administered to the site of a wound, as a coating on a prosthetic device or incorporated into a matrix, thus mediating the binding of integrin-expressing cells and increasing the rate of wound healing. Methods of incorporating a peptide of the present invention into an artificial extracellular matrix are described in WO90/06767, which is herein incorporated by reference.

The invention provides pharmaceutical compositions comprising a peptide of the present invention and a pharmaceutically acceptable carrier. Pharmaceutically acceptable carriers are well known in the 30 art and include aqueous solutions such as physiologically buffered saline or other solvents or vehicles such as glycols, glycerol, oils such as olive oil or injectable organic esters.

A pharmaceutically acceptable carrier can contain physiologically acceptable compounds that act, for example, to stabilize the peptide of the present invention or increase the absorption of the peptide. Such physiologically acceptable compounds include, for example, carbohydrates, such as glucose, sucrose or dextrans, antioxidants, such as ascorbic acid or glutathione, chelating agents, low molecular weight proteins or other stabilizers or excipients. One skilled in the art would know that the choice of a pharmaceutically acceptable carrier, including a physiologically acceptable compound, depends, for example, on the route of administration of the integrin-binding peptide and on the particular physico-chemical characteristics of the specific peptide.

The invention further relates to methods of administering a pharmaceutical composition comprising a peptide of the present invention to a subject in order, for example, to promote wound healing in the subject or to prevent the spread and infiltration of metastatic tumor cells. One skilled in the art would know that a pharmaceutical composition comprising a peptide of the present invention can be administered to a subject having a wound or a cancer that is likely to metastasize by various routes, depending on the specific pathologic condition. For example, where the treatment is localized such as for inducing healing of a wound, a pharmaceutical composition comprising a peptide of the present invention can be suspended or dissolved in the appropriate pharmaceutically acceptable carrier and administered topically. Alternatively, where treatment is systemic due, for example, to the presence in the subject of metastatic tumor cells, the composition can be administered orally or parenterally, such as intravenously, intramuscularly, subcutaneously, intraorbitally, intracapsularly, intraperitoneally or intracisternally.

The total effective amount of a peptide of the present invention can be administered to a subject as a single dose, either as a bolus or by infusion over a relatively short period of time, or can be administered using a fractionated treatment protocol, in which the multiple doses are administered over a more prolonged period of time. One skilled in the art would know that the concentration of a peptide of the present invention required to obtain an effective dose in a subject depends on many factors including the age and general health of the subject as well as the route of administration and the number of treatments to be administered. In view of these factors, the skilled artisan would adjust the dose so as to provide an effective dose for a particular use.

The peptides of the present invention, in particular those peptides having specificity for the $\alpha_5\beta_1$ integrin, can also be used for identifying and isolating cell types expressing certain integrins. Cells expressing the $\alpha_5\beta_1$ integrin, for example, can be identified and isolated from a tissue by coating a surface or column with a peptide having specificity for the $\alpha_5\beta_1$ integrin, allowing the cells to bind to the surface or column, then eluting the cells from the surface or column, for example, using low pH buffer or EDT-containing buffer. This method may be particularly useful for isolating subsets of the lymphocyte population which express various integrins. Such peptide columns can also be used to isolate integrins as purified proteins as described in Pytela et al., *Methods Enzy.* 82:803–831 (1987) which is incorporated herein by reference.

The invention will now be described in greater detail by reference to the following examples. These examples are intended to illustrate but not limit the invention.

EXAMPLE I

Materials and Methods

Peptides were synthesized on an Applied Biosystems Model 430A synthesizer (Foster City, Calif.) by standard Merrifield solid phase synthesis protocols and t-butoxycarbonyl chemistry. Linear peptides were cyclized by oxidizing with 0.01 M $K_3Fe(CN)_6$ at pH 8.4 and purified by reverse phase HPLC. Cyclic peptides were linearized by reduction followed by alkylation. Reduction and alkylation was performed according to the following method. Five mg of the cyclic peptide were incubated for 1 hour at 37° C. in 0.1 M Tris buffer (pH 8) containing 8 M urea and 100-fold molar excess of dithiothreitol. After adding 200-fold molar excess of iodoacetamide the incubation was continued for further 30 minutes in the dark. The peptide was dialyzed extensively against water using a membrane with 500 molecular weight cut off. The recovery of the peptide after dialysis was 43% as determined by UV absorbance.

Polyclonal antibodies against the cytoplasmic tails of $\alpha_5$, $\alpha_v$ and $\beta_3$ subunits were prepared by immunizing rabbits with synthetic peptides representing the cytoplasmic tails, according to the methods described in Vogel et al., *J. Cell. Biol.* 121:461–468 (1993), Freed et al., *EMBO J* 8: 2955–2965 (1989), and Giancotti et al., *Cell* 60: 849–859 (1990), all of which are incorporated by reference. The antibodies were affinity purified using the immunizing peptides using methods known to one skilled in the art, see, for example, Harlow et al., Antibodies: A Laboratory Manual, Cold Spring Harbor (1989), which is herein incorporated by reference.

*Escherichia coli* strain K91kan was a gift from Dr. G. Smith (University of Missouri, Columbia, Mo.). Human plasma fibronectin was obtained from the Finnish Red Cross and was iodinated as described Morla and Ruoslahti, *J. Cell Biol.* 118:421–429 (1992), which is herein incorporated by reference. Vitronectin was obtained from Telios Pharmaceuticals (San Diego, Calif.).

The $\alpha_5\beta_1$ and $\alpha_v\beta_3$ integrins were isolated from human placenta as described in Pytela et al., *PNAS USA.* 82:5766–5770 (1987), which is incorporated herein by reference.

EXAMPLE II

Fibronectin Binding Assay

Polyclonal antibodies against the cytoplasmic tails of $\alpha_5$, $\alpha_v$ and $\beta_3$ subunits were prepared as described in Example I above.

Microtiter wells were coated with anti-$\alpha_5$ specific antibody by incubating overnight at an antibody concentration of 10 μg/ml, followed by BSA. $\alpha_5\beta_1$ integrin then was bound to $\alpha_5$ specific antibody-coated wells by incubating 300 μl of a placental extract per well in TBS buffer containing 0.1 M octylglucoside, 1 mM $CaCl_2$, 1 mM $MnCl_2$ and proteinase inhibitors overnight at 4° C. according to Pytela et al., *Methods Enzymol* 144: 475–489 (1987), which is herein incorporated by reference. Alternatively, the $\alpha_{5\beta 1}$ integrin was directly coated on plastic as described above. The wells were extensively washed with TBS containing 0.1% NP-40™. $^{125}$I-labeled fibronectin (100,000 cpm per well) was incubated in the presence of competing peptides for 1 hour at 25° C. in 100 μl volume of TBS containing 0.1% NP-40™ detergent and 1 mM MnCl$_2$. After repeated washing, the radioactivity remaining bound was quantitated with a gamma counter.

EXAMPLE III

Cell Attachment Assay

This assay was performed to determine the integrin-binding specificity of the peptides of the present invention. Cell lines expressing different integrins were used to examine peptide inhibition of integrin functions.

CHO cell lines expressing $\alpha_5\beta_1$ (the B2/α27 clone, as described in Bauer et al., *J. Cell. Biol.* 116:477–487 (1992)), or CHO cell lines expressing $\alpha_v\beta_1$ (B2/v7 clone, described in Zhang et al., *J. Cell. Biol.* 122:235–242 (1993)) were used in these assays. Cell lines expressing fibronectin-binding integrins were used to determine peptide activities against these integrins in the cell attachment assay described in Ruoslahti et al. *Methods Enzymol.* 144:803–831 (1982). The vitronectin-binding integrins $\alpha_v\beta_5$ and $\alpha_v\beta_3$ were assayed using the cell lines HT29 and IMR90, respectively, which were described in Koivunen et al. *J. Biol. Chem.* 268:205–210 (1993).

Human plasma fibronectin and vitronectin were iodinated as described in Morla and Ruoslahti, *J. Cell Biol.* 118:421–429 (1992), which is incorporated herein by reference. Microliter wells were coated with fibronectin or vitronectin at a concentration that resulted in 50–70% maximum attachment for each cell type (B2/α27, 2 μg/ml; B2/v7, 4 μg/ml; HT29, 8 μg/ml; IMR90, 1 μg/ml). The input ell number was approximately 2×10$^4$ and attachment was quantitated by staining with 0.1% amido black.

EXAMPLE IV

Determination of Relative Binding Affinities of Integrin-Binding Peptides

To test the affinities of peptides relative to each other, the following peptides were synthesized: PKRGDL (SEQ ID NO 20), MRGDLR (SEQ ID NO 21), GARGDFWQGA (SEQ ID NO 22) and GARGDHWTGA (SEQ ID NO 23). The last two peptides contain flanking glycine-alanine sequences.

None of these linear peptides proved to be more efficient in binding than the standard fibronectin-derived peptide GRDGSP, first described in Pierschbacher and Ruoslahti, *Nature* 309: 30–33 (1984), which is herein incorporated by reference, in inhibiting the binding of an RGD-containing phage (CRGDCL) to $\alpha_5\beta_1$ in the phage attachment assay described below. Some of these linear peptides were then compared to a cyclic peptide.

The cyclic peptide GAC*RGDC*LGA, (hereinafter designated GACRGDCLGA (SEQ ID NO:03)) wherein "*" indicates the cysteine residues involved in forming the disulfide bridge, was synthesized as described in the Example above, and tested against the linear GRGDSP (SEQ ID NO:02) peptide, as well as the peptides NGRAHA (SEQ ID NO:04) and GATIRSVDGA (SEQ ID NO:05) using the phage assay described below.

$\alpha_5\beta_1$ integrin was bound to microliter wells precoated with anti-$\alpha_5$ antibodies as described in Pytela et al., *Cell* 40:191–198 (1985) and Pytela et al., *PNAS USA* 82:5766–5770 (1987)),: The CRGDCL (SEQ ID NO:01)-containing phage was obtained from the peptide-displaying phage library constructed as described by Scott and Smith, *Science* 249:1738–1740 (1990). CRGDCL-displaying phage were incubated for 1 hour in the presence of various concentrations of the peptides to be tested in microtiter wells coated with the $\alpha_5\beta_1$ integrin. The input of phage containing the CRGDCL (SEQ ID NO:01) peptide was 2×10$^{12}$ TU per well. Specific binding was quantitated by added K9lkan bacteria directly to the wells and growing the bacteria overnight at room temperature in the presence of tetracycline as described in Smith and Scott, *Meth. Enzymol.* 217:228–257 (1993), which is incorporated herein by reference. The results are shown in FIG. 1. The data represent means from duplicate wells.

In contrast to the linear peptides, the cyclic peptide GACRDGCLGA (SEQ ID NO:03 ) was about 10 times more potent than the linear GRGDSP (SEQ ID NO:02) as shown by the IC$_{50}$ (half-maximal inhibitory concentration) values of 2×10$^{-7}$ M (GRGDSP) and 2×10$^{-8}$ M (GACRDGCLGA (SEQ ID NO:03)). NGRAHA (SEQ ID NO:04) inhibited with an IC$_{50}$ of 3×10$^{-5}$ in the phage assay, but GATIRSVDGA (SEQ ID NO:05) was essentially inactive.

Next, three of these four peptides were compared for efficiencies in inhibiting binding of $^{125}$I-labeled fibronectin to immobilized $\alpha_5\beta_1$, according to the fibronectin binding assay described in the Example above. This is shown in FIG. 2. Anti-$\alpha_5$ antibodies were used to tether $\alpha_5\beta_1$ onto microliter wells. $^{125}$I-labeled fibronectin was incubated in the coated wells in the presence of competing peptides for 1 hour. After washing, the radioactivity that remained bound was determined. The data represent means from duplicate wells.

As shown in FIG. 2, there is a 10-fold difference in the activities of the cyclic peptide and linear GRGDSP. The peptide ligand NGRAHA (SEQ ID NO:04) was also active in the fibronectin binding assay. In another experiment, reduction and alkylation of the disulfide bond in GACRGDCLGA (SEQ ID NO:03) caused a 10-fold decrease of activity. Reduction and alkylation was performed as described in Example I above.

Figure 3:
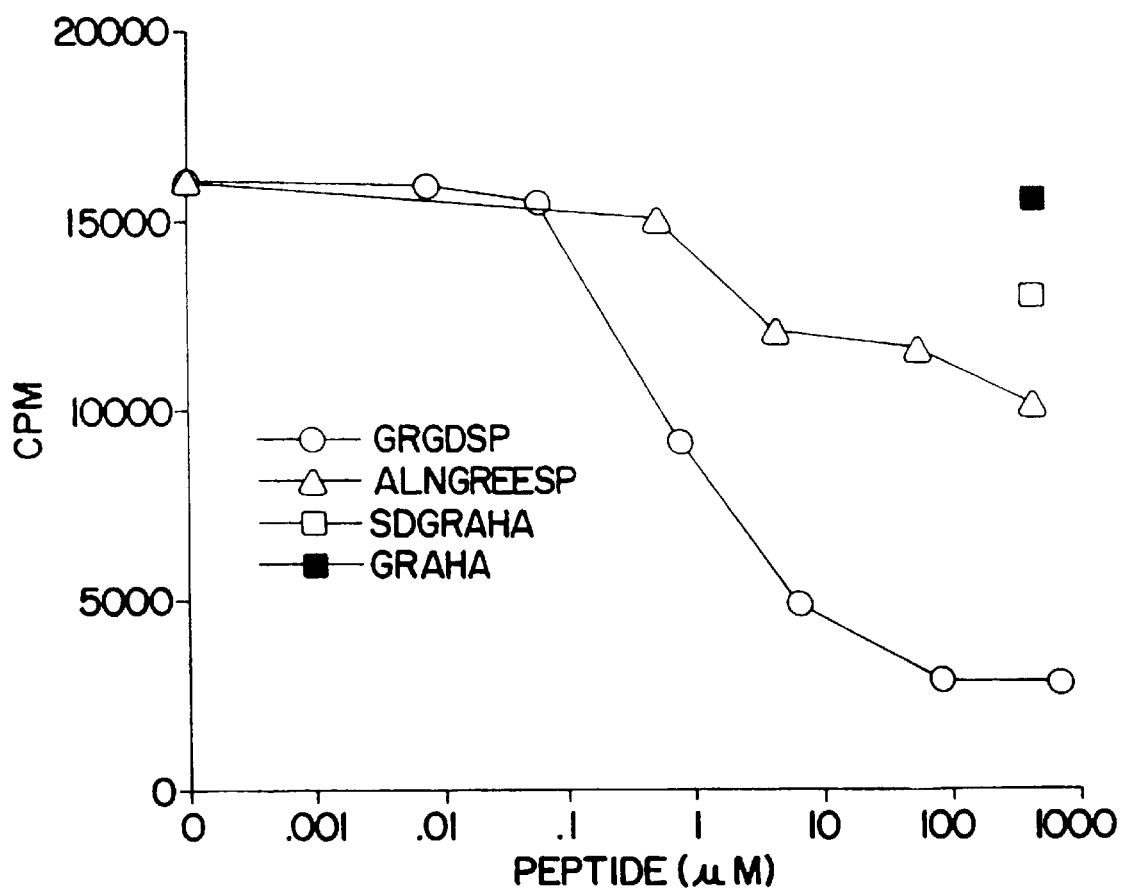
FIG. 3 shows the inhibition of binding of fibronectin to $\alpha_5\beta_1$ integrin by the peptides GRGDSP, ALNGREESP (SEQ ID NO 6), SDGRAHA (SEQ ID NO 7) and GRAHA (SEQ ID NO 8).

In order to localize the activity in the NGRAHA (SEQ ID NO:04) sequence, a peptide in which the asparagine residue was deleted, GRAHA (SEQ ID NO:08) was synthesized. Binding of $^{125}$I-labeled fibronectin was tested as described in the Example above, in the presence of competing peptides. The GRAHA (SEQ ID NO:08) peptide was completely inactive, as shown in FIG. 3. Another synthetic peptide DGRAHA (SEQ ID NO:11) that contained an aspartate instead of asparagine, however was equally active as NGRAHA (SEQ ID NO:04). Next, a serine residue was included at the amino terminus of the peptide. The SDGRAHS (SEQ ID NO:07) peptide, however, was essentially devoid of activity, as is shown In FIG. 3. A peptide derived from the cell-binding region of fibronectin that contains the NGR sequence, ALNGREESP (SEQ ID NO:06), was active, but less so than NGRAHA (SEQ ID NO:04).

The relative affinity of the cyclic peptide GACRGD-CLGA (SEQ ID NO:03) peptide was also determined by inhibition of a linear phage-displayed peptide binding $\alpha_5\beta_1$ integrin. Phage carrying the insert ELRGDGW (SEQ ID NO 24) were added together with various concentrations of the cyclic peptide GACRGDCLGA (SEQ ID NO:03) into microliter wells coated with the $\alpha_5\beta_1$ integrin and incubated for 1 hour at room temperature. The 15 phage which remained bound to the wells were quantitated by growing the K9lkan bacteria in the wells overnight at room temperature in the presence of tetracycline. The absorbance that indicates the growth of bacteria infected with phage was measured at 600 nm with an ELISA reader. The results indicate inhibition of binding of ELRGDGW (SEQ ID NO:24)-containing phage to $\alpha_5\beta_1$ integrin by GACRGD-CLGA (SEQ ID NO:03) with an IC$_{50}$ value of approximately $5\times10^{-7}$ M.

EXAMPLE V

Ability of Peptides to Bind to the $\alpha_v\beta_3$ Integrin

Selected peptides were studied for their ability to bind to the $\alpha_v\beta_3$ integrin by using integrin bound on anti-$\alpha_v$ or anti-$\beta_3$ antibody coating. Microliter wells were coated with $\beta_3$ antibodies to bind specifically the $\alpha_v\beta_3$ integrin. The input of CRGDCL (SEQ ID NO:01)-containing phage and NGRAHA (SEQ ID NO:04)-containing phage were $2\times10^{12}$ and $5\times10^{12}$ TU per well, respectively. The bound phage were eluted with low pH buffer and quantitated by infection of bacteria as described above. The IC$_{50}$ values are means from duplicate wells. ND means not determined.

The peptides CRGDCL (SEQ ID NO:01), NGRAHA (SEQ ID NO:04), PKRGDL (SEQ ID NO:20) and SRRGDL (SEQ ID NO:25). (SEQ ID NO 25) each bound to $\alpha_v\beta_3$. Table III shows the IC$_{50}$ values for the peptides when CRGDCL (SEQ ID NO:01)-phage and NGRAHA (SEQ ID NO:04)-phage were used in the assay. The cyclic peptide GACRGDCLGA (SEQ ID NO:03) with an IC$_{50}$ of $1\times10^{-7}$ M inhibited the CRGDCL (SEQ ID NO:01)-phage attachment 10-fold better than the peptide GRGDSP. The peptides NGRAHA (SEQ ID NO:04) and GATIRSVDGA (SEQ ID NO:05) were weakly inhibitory at high concentrations (greater than 100 μM), as shown in Table III below.

TABLE III

INHIBITION OF PHAGE BINDING TO $\alpha_v\beta_3$ BY RGD-CONTAINING PEPTIDES

| PEPTIDE | CRGDCL-phage IC$_{50}$ (M) | NGRAHA-phage |
|---|---|---|
| GACRGDCLGA (SEQ ID NO: 03) | $1 \times 10^{-7}$ | ND |
| GRGDSP (SEQ ID NO: 02) | $1 \times 10^{-6}$ | $2 \times 10^{-8}$ |
| NGRAHA (SEQ ID NO: 04) | $2 \times 10^{-4}$ | $3 \times 10^{-5}$ |
| GATIRSVDGA (SEQ ID NO: 05) | $\sim 10^{-4}$ | ND |
| DGRAHA (SEQ ID NO: 11) | ND | $1 \times 10^{-4}$ |
| SDGR (SEQ ID NO: 12) | ND | $>10^{-4}$ |

EXAMPLE VI

Effect of Peptides on Cell Attachment

Selected peptides were tested for inhibitory activity in cell attachment assays. The assays are described in detail in the Example above. The cells used in the various experiments were: (A) $\alpha_5$-transfected CHO cells B2/α27 ($\alpha_5\beta_1$); $\alpha_v$-transfected CHO cells 32/v7 ($\alpha_v\beta_1$); (C) HT29 cells ($\alpha_v\beta_5$); (D) IMR90 cells ($\alpha_v\beta_3$). The cells were allowed to attach to microliter wells coated with fibronectin (A,B) or vitronectin (C,D) in the presence of various concentrations of the peptides, as described in the Example above. Attached cells were fixed and stained as described in the Example above. The data represent means ±S.D. from triplicate wells.

Figure 4A:
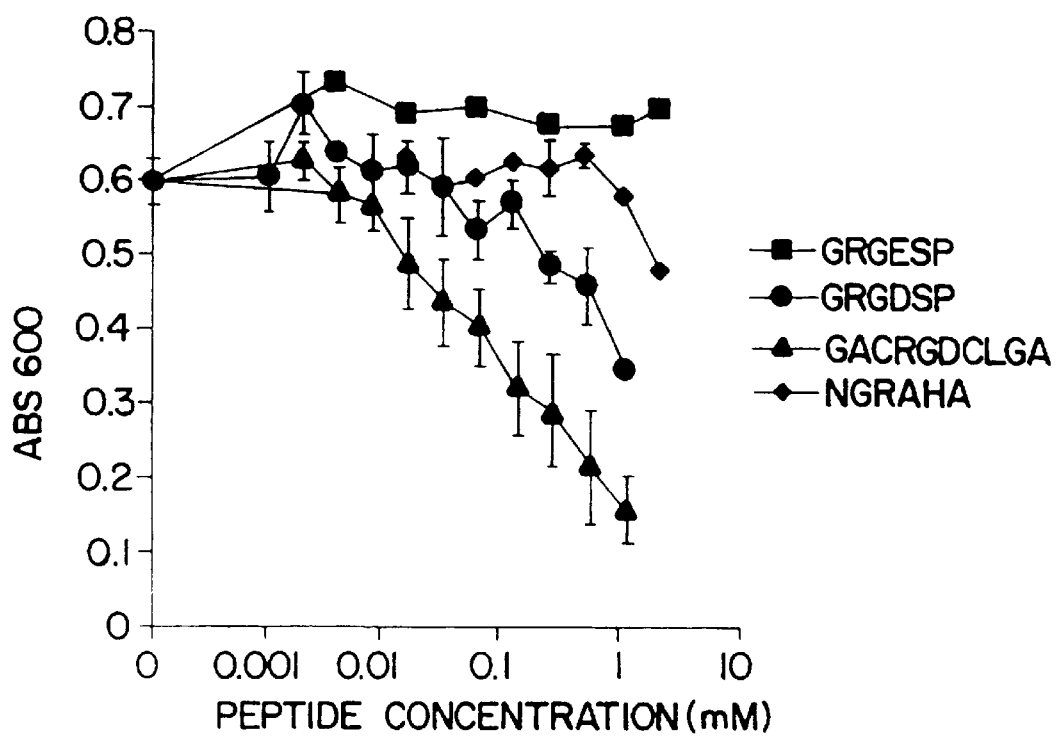
FIG. 4A shows the inhibition of binding of $\alpha_5$-transfected CHO cells ($a_5\beta_1$) to fibronectin in the presence of GRGESP (SEQ ID NO 9), GRGDSP (SEQ ID NO:02), GACRGDCLGA (SEQ ID NO:03) and NGRAHA (SEQ ID NO:04)
Figure 4B:
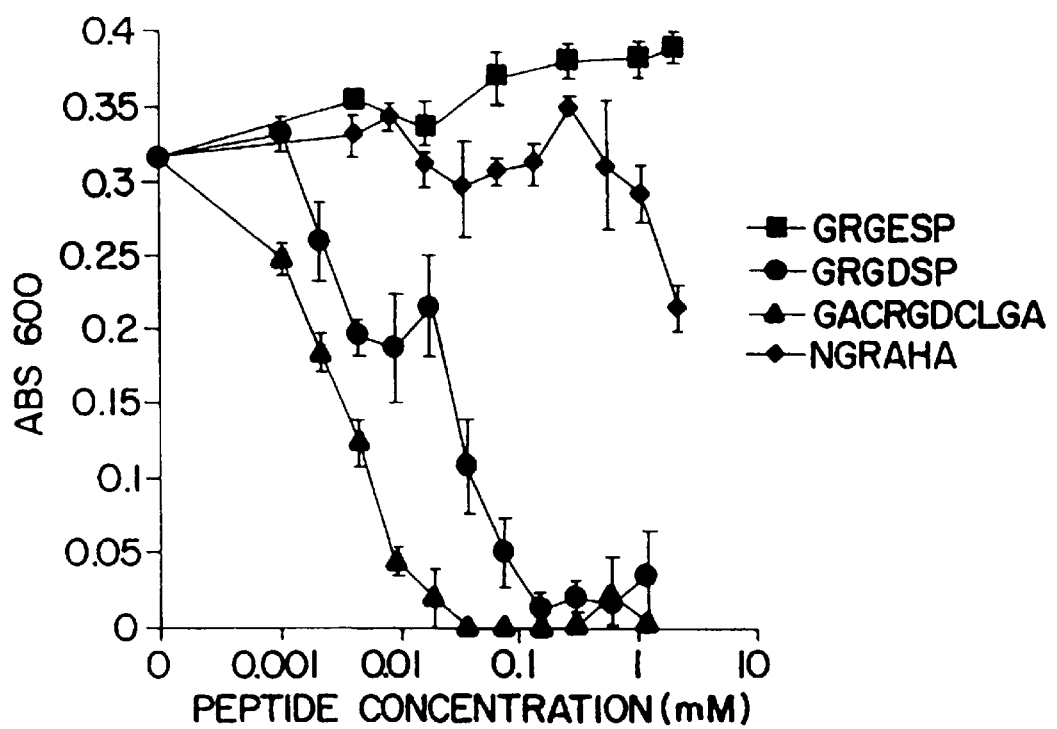
FIG. 4B shows the inhibition of binding of $\alpha_v$-transfected CHO cells ($\alpha_v\beta_1$) to fibronectin in the presence of the same peptides.

The cyclic GACRGDCLGA (SEQ ID NO:03), peptide had an IC$_{50}$ of $1\times10^{-4}$ M and was about a 10-fold better inhibitor of $\alpha_5\beta_1$-mediated cell attachment to fibronectin than the linear GRGDSP peptide as shown in FIG. 4A. The NRGAHA (SEQ ID NO:4), peptide could partially inhibit at a concentration of 2.5 mM.

Figure 4C:
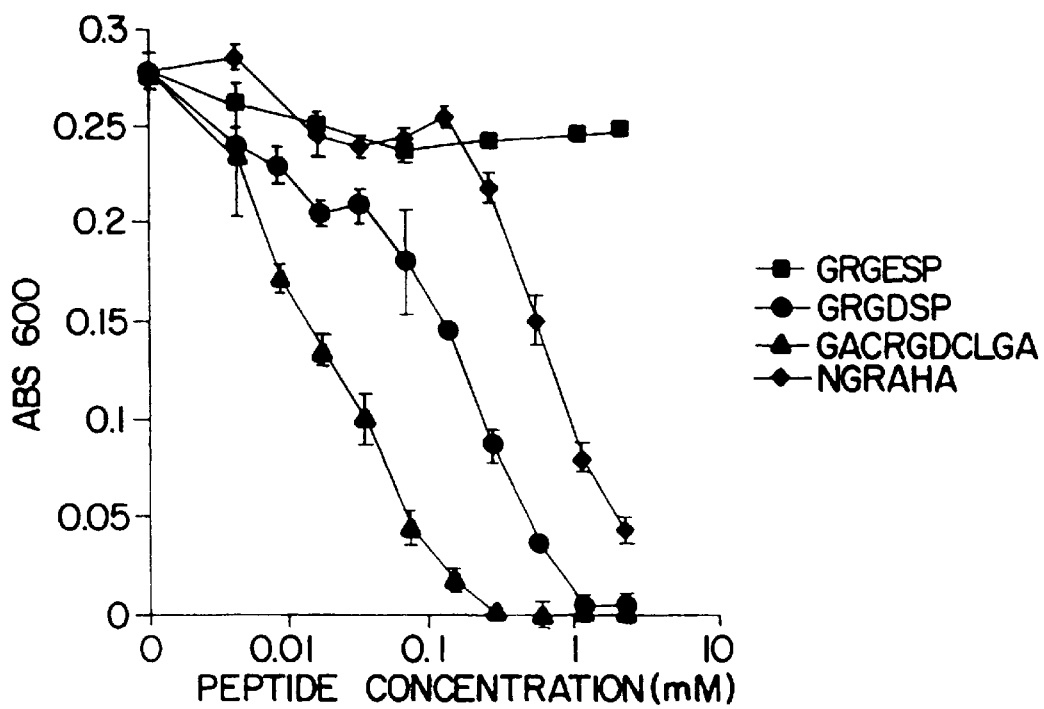
FIG. 4C shows the inhibition of binding of HT29 cells ($\alpha_v\beta_5$) to vitronectin in the presence of the same peptides.
Figure 4D:
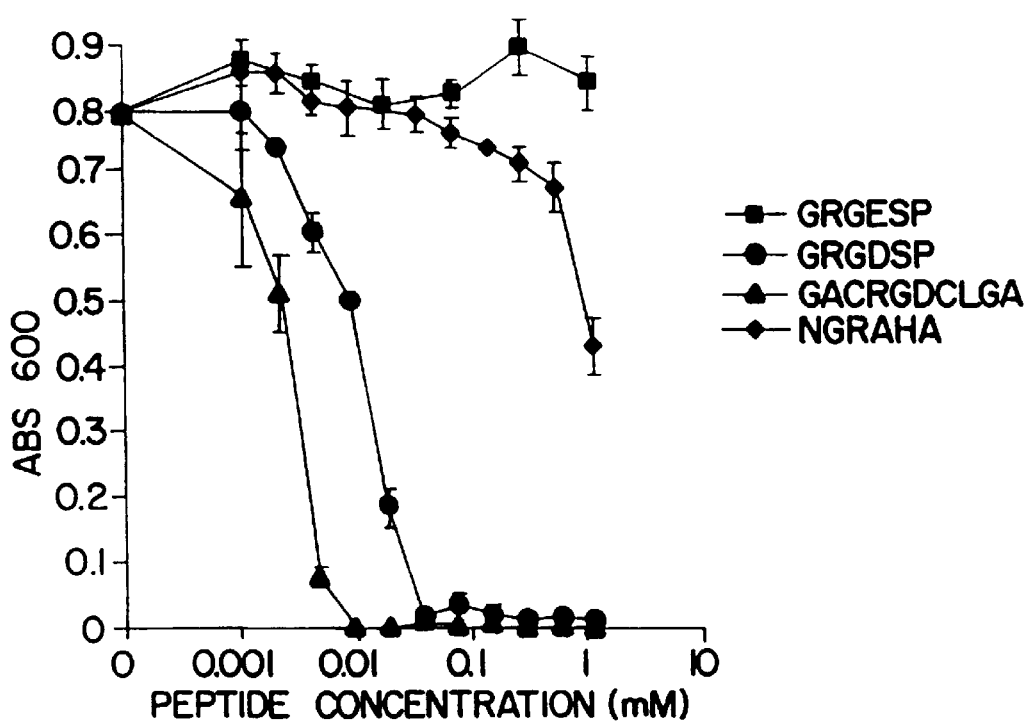
FIG. 4D shows the inhibition of binding of IMR90 cells ($\alpha_v\beta_3$) to vitronectin in the presence of the same peptides.

A similar 10-fold activity difference between the GACRGDCLGA (SEQ ID NO:03) and GRGDSP (SEQ ID NO:02), peptides was found in cell attachment mediated by the $\alpha_v\beta_1$ (FIG. 4B) and $\alpha_v\beta_5$ and $\alpha_v\beta_3$ integrins (FIG. 4C and 4D).

The NGRAHA (SEQ ID NO:04) peptide could also block cell attachment mediated by the three $\alpha_v$-integrins. It inhibited most efficiently in the assay measuring the $\alpha_v\beta_5$-integrin. A similar peptide, DGRAHA (SEQ ID NO:11) was even more active against $\alpha_v\beta_5$ showing an IC$_{50}$ equal to the standard GRGDSP (SEQ ID NO:02). By contrast, in another experiment, the fibronectin-derived ALNGREESP (SEQ ID NO:06) peptide was only weakly inhibitory at high concentrations 5 mM) and GRAHA (SEQ ID NO:08), was devoid of activity in this assay.

While the invention has been described in detail with reference to presently preferred embodiments, it is understood that various modifications can be made without departing from the spirit of the invention. Accordingly, the invention is limited only by the following claims.

We claim:

1. A purified peptide comprising an amino acid sequence, Asn-Gly-Arg, -NGR-, wherein said peptide has fibronectin- and vitronectin- integrin binding activity and a total number of amino acid residues equal to or less than twenty.

* * * * *

UNITED STATES PATENT AND TRADEMARK OFFICE
CERTIFICATE OF CORRECTION

PATENT NO.    : 6,177,542 B1
DATED         : January 23, 2001
INVENTOR(S)   : Ruoslahti et al.

It is certified that error appears in the above-identified patent and that said Letters Patent is hereby corrected as shown below:

Column 21,
Line 32, please delete "-NGR-" replace therefor with -- -NGR, --.

Column 22,
Line 30, please delete "vitronectin-" replace therefor with -- vitronectin --.

Signed and Sealed this

Thirteenth Day of July, 2004

JON W. DUDAS
*Acting Director of the United States Patent and Trademark Office*

SEQUENCE LISTING (1) GENERAL INFORMATION:

(iii) NUMBER OF SEQUENCES: 26

(2) INFORMATION FOR SEQ ID NO:1:

(i) SEQUENCE CHARACTERISTICS:
        (A) LENGTH: 6 amino acids
        (B) TYPE: amino acid
        (D) TOPOLOGY: both (xi) SEQUENCE DESCRIPTION: SEQ ID NO:1:

Cys Arg Gly Asp Cys Leu
1               5

(2) INFORMATION FOR SEQ ID NO:2:

(i) SEQUENCE CHARACTERISTICS:
        (A) LENGTH: 6 amino acids
        (B) TYPE: amino acid
        (D) TOPOLOGY: linear (xi) SEQUENCE DESCRIPTION: SEQ ID NO:2:

Gly Arg Gly Asp Ser Pro
1               5

(2) INFORMATION FOR SEQ ID NO:3:

(i) SEQUENCE CHARACTERISTICS:
        (A) LENGTH: 10 amino acids
        (B) TYPE: amino acid
        (D) TOPOLOGY: both (xi) SEQUENCE DESCRIPTION: SEQ ID NO:3:

Gly Ala Cys Arg Gly Asp Cys Leu Gly Ala
1               5                   10

(2) INFORMATION FOR SEQ ID NO:4:

(i) SEQUENCE CHARACTERISTICS:
        (A) LENGTH: 6 amino acids
        (B) TYPE: amino acid
        (D) TOPOLOGY: both (xi) SEQUENCE DESCRIPTION: SEQ ID NO:4:

Asn Gly Arg Ala His Ala
1               5

(2) INFORMATION FOR SEQ ID NO:5:

(i) SEQUENCE CHARACTERISTICS:
        (A) LENGTH: 10 amino acids
        (B) TYPE: amino acid
        (D) TOPOLOGY: linear (xi) SEQUENCE DESCRIPTION: SEQ ID NO:5:

Gly Ala Thr Ile Arg Ser Val Asp Gly Ala
1               5                   10

(2) INFORMATION FOR SEQ ID NO:6:

(i) SEQUENCE CHARACTERISTICS:
        (A) LENGTH: 9 amino acids
        (B) TYPE: amino acid
        (D) TOPOLOGY: linear (xi) SEQUENCE DESCRIPTION: SEQ ID NO:6:

Ala Leu Asn Gly Arg Glu Glu Ser Pro
1               5

(2) INFORMATION FOR SEQ ID NO:7:

(i) SEQUENCE CHARACTERISTICS:
        (A) LENGTH: 7 amino acids
        (B) TYPE: amino acid
        (D) TOPOLOGY: linear (xi) SEQUENCE DESCRIPTION: SEQ ID NO:7:

Ser Asp Gly Arg Ala His Ala
1               5

(2) INFORMATION FOR SEQ ID NO:8:

(i) SEQUENCE CHARACTERISTICS:
        (A) LENGTH: 5 amino acids
        (B) TYPE: amino acid
        (D) TOPOLOGY: linear (xi) SEQUENCE DESCRIPTION: SEQ ID NO:8:

Gly Arg Ala His Ala
1               5

(2) INFORMATION FOR SEQ ID NO:9:

(i) SEQUENCE CHARACTERISTICS:
        (A) LENGTH: 6 amino acids
        (B) TYPE: amino acid
        (D) TOPOLOGY: linear (xi) SEQUENCE DESCRIPTION: SEQ ID NO:9:

Gly Arg Gly Glu Ser Pro
1               5

(2) INFORMATION FOR SEQ ID NO:10:

(i) SEQUENCE CHARACTERISTICS:
        (A) LENGTH: 5 amino acids
        (B) TYPE: amino acid
        (D) TOPOLOGY: both (xi) SEQUENCE DESCRIPTION: SEQ ID NO:10:

Cys Arg Gly Asp Cys
1               5

(2) INFORMATION FOR SEQ ID NO:11:

(i) SEQUENCE CHARACTERISTICS:
        (A) LENGTH: 6 amino acids
        (B) TYPE: amino acid
        (D) TOPOLOGY: both (xi) SEQUENCE DESCRIPTION: SEQ ID NO:11:

Asp Gly Arg Ala His Ala
1               5

(2) INFORMATION FOR SEQ ID NO:12:

(i) SEQUENCE CHARACTERISTICS:
        (A) LENGTH: 4 amino acids
        (B) TYPE: amino acid
        (D) TOPOLOGY: linear (xi) SEQUENCE DESCRIPTION: SEQ ID NO:12:

Ser Asp Gly Arg
1

(2) INFORMATION FOR SEQ ID NO:13:

(i) SEQUENCE CHARACTERISTICS:
        (A) LENGTH: 8 amino acids
        (B) TYPE: amino acid
        (D) TOPOLOGY: circular (xi) SEQUENCE DESCRIPTION: SEQ ID NO:13:

Cys Val Leu Asn Gly Arg Met Glu
1           5

(2) INFORMATION FOR SEQ ID NO:14:

(i) SEQUENCE CHARACTERISTICS:
        (A) LENGTH: 6 amino acids
        (B) TYPE: amino acid
        (D) TOPOLOGY: linear (xi) SEQUENCE DESCRIPTION: SEQ ID NO:14:

Arg Cys Asp Val Val Val
1           5

(2) INFORMATION FOR SEQ ID NO:15:

(i) SEQUENCE CHARACTERISTICS:
        (A) LENGTH: 6 amino acids
        (B) TYPE: amino acid
        (D) TOPOLOGY: linear (xi) SEQUENCE DESCRIPTION: SEQ ID NO:15:

Ser Leu Ile Asp Ile Pro
1           5

(2) INFORMATION FOR SEQ ID NO:16:

(i) SEQUENCE CHARACTERISTICS:
        (A) LENGTH: 6 amino acids
        (B) TYPE: amino acid
        (D) TOPOLOGY: linear (xi) SEQUENCE DESCRIPTION: SEQ ID NO:16:

Thr Ile Arg Ser Val Asp
1           5

(2) INFORMATION FOR SEQ ID NO:17:

(i) SEQUENCE CHARACTERISTICS:
        (A) LENGTH: 4 amino acids
        (B) TYPE: amino acid
        (D) TOPOLOGY: linear (xi) SEQUENCE DESCRIPTION: SEQ ID NO:17:

Lys Arg Gly Asp
1

(2) INFORMATION FOR SEQ ID NO:18:

(i) SEQUENCE CHARACTERISTICS:
        (A) LENGTH: 4 amino acids
        (B) TYPE: amino acid
        (D) TOPOLOGY: linear (xi) SEQUENCE DESCRIPTION: SEQ ID NO:18:

Arg Arg Gly Asp
1

(2) INFORMATION FOR SEQ ID NO:19:

(i) SEQUENCE CHARACTERISTICS:
        (A) LENGTH: 4 amino acids
        (B) TYPE: amino acid
        (D) TOPOLOGY: linear (xi) SEQUENCE DESCRIPTION: SEQ ID NO:19:

Arg Gly Asp Leu
1

(2) INFORMATION FOR SEQ ID NO:20:

(i) SEQUENCE CHARACTERISTICS:
        (A) LENGTH: 6 amino acids
        (B) TYPE: amino acid
        (D) TOPOLOGY: linear (xi) SEQUENCE DESCRIPTION: SEQ ID NO:20:

Pro Lys Arg Gly Asp Leu
1          5

(2) INFORMATION FOR SEQ ID NO:21:

(i) SEQUENCE CHARACTERISTICS:
        (A) LENGTH: 6 amino acids
        (B) TYPE: amino acid
        (D) TOPOLOGY: linear (xi) SEQUENCE DESCRIPTION: SEQ ID NO:21:

Met Arg Gly Asp Leu Lys
1          5

(2) INFORMATION FOR SEQ ID NO:22:

(i) SEQUENCE CHARACTERISTICS:
        (A) LENGTH: 10 amino acids
        (B) TYPE: amino acid
        (D) TOPOLOGY: linear (xi) SEQUENCE DESCRIPTION: SEQ ID NO:22:

Gly Ala Arg Gly Asp Phe Trp Gln Gly Ala
1          5                10

(2) INFORMATION FOR SEQ ID NO:23:

(i) SEQUENCE CHARACTERISTICS:
        (A) LENGTH: 10 amino acids
        (B) TYPE: amino acid
        (D) TOPOLOGY: linear (xi) SEQUENCE DESCRIPTION: SEQ ID NO:23:

Gly Ala Arg Gly Asp His Trp Thr Gly Ala
1          5                10

(2) INFORMATION FOR SEQ ID NO:24:

(i) SEQUENCE CHARACTERISTICS:
        (A) LENGTH: 7 amino acids
        (B) TYPE: amino acid
        (D) TOPOLOGY: linear (xi) SEQUENCE DESCRIPTION: SEQ ID NO:24:

```
Glu Leu Arg Gly Asp Gly Trp
1               5
```

(2) INFORMATION FOR SEQ ID NO:25:

(i) SEQUENCE CHARACTERISTICS:
        (A) LENGTH: 6 amino acids
        (B) TYPE: amino acid
        (D) TOPOLOGY: linear (xi) SEQUENCE DESCRIPTION: SEQ ID NO:25:

```
Ser Arg Arg Gly Asp Leu
1               5
```

(2) INFORMATION FOR SEQ ID NO:26:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (xi) SEQUENCE DESCRIPTION: SEQ ID NO:26:

```
Cys Arg Gly Asp Cys Ala
1               5
```